United States Patent
Asano et al.

(10) Patent No.: US 9,568,411 B2
(45) Date of Patent: *Feb. 14, 2017

(54) EXHAUST GAS ANALYSIS SYSTEM AND EXHAUST GAS ANALYSIS PROGRAM

(71) Applicant: HORIBA, Ltd., Kyoto-shi, Kyoto (JP)

(72) Inventors: Ichiro Asano, Kyoto (JP); Masayoshi Shinohara, Kyoto (JP); Kazuo Hanada, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/867,219

(22) Filed: Sep. 28, 2015

(65) Prior Publication Data

US 2016/0018309 A1    Jan. 21, 2016

Related U.S. Application Data

(63) Continuation of application No. 13/824,507, filed as application No. PCT/JP2011/070864 on Sep. 13, 2011, now Pat. No. 9,188,506.

(30) Foreign Application Priority Data

Sep. 24, 2010    (JP) .................. 2010-214546

(51) Int. Cl.
  *G01N 15/06* (2006.01)
  *G01N 1/22* (2006.01)
  (Continued)

(52) U.S. Cl.
  CPC .............. *G01N 15/06* (2013.01); *G01M 15/10* (2013.01); *G01M 15/102* (2013.01);
  (Continued)

(58) Field of Classification Search
  CPC ....... G01M 15/10; G01N 1/2252; G01N 15/06
  See application file for complete search history.

(56) References Cited

U.S. PATENT DOCUMENTS 3,774,442 A    11/1973    Gustavsson
4,034,611 A    7/1977    Horling
(Continued)

FOREIGN PATENT DOCUMENTS

CN    101334349 A    12/2008
CN    101672732 A    3/2010
(Continued)

OTHER PUBLICATIONS

International Search Report dated Nov. 15, 2011 for International Application No. PCT/JP2011/070864, filed Sep. 13, 2011, 4 pgs.
(Continued)

*Primary Examiner* — Laura Martin
*Assistant Examiner* — Alex Devito
(74) *Attorney, Agent, or Firm* — Brooks Kushman P.C.

(57) ABSTRACT

The present invention is one that, even while cooling exhaust gas without dilution, makes it possible to accurately measure particle concentration, and provided with: a particle concentration measurement device; a sampling cooling pipe that cools the exhaust gas collected from an exhaust gas transfer pipe to a measurable temperature of the particle concentration measurement device without dilution, and introduces the cooled exhaust gas into the particle concentration measurement device; a temperature sensor that detects temperature of the exhaust gas flowing into an exhaust gas inlet; and a calculation device that, from the detected temperature by the temperature sensor and the temperature of the exhaust gas introduced into the particle concentration measurement device, corrects measured particle concentration by the particle concentration measure-
(Continued)

ment device in real time to calculate the particle concentration of the exhaust gas flowing through the exhaust gas transfer pipe.

7 Claims, 3 Drawing Sheets

(51) Int. Cl.
    *G01M 15/10*     (2006.01)
    *G01N 25/22*     (2006.01)

(52) U.S. Cl.
    CPC ........... *G01N 1/2252* (2013.01); *G01N 25/22* (2013.01); *G01N 2001/2282* (2013.01)

(56) References Cited

U.S. PATENT DOCUMENTS

| | | |
|---|---|---|
| 4,100,801 A | 7/1978 | LeMay |
| 4,655,089 A | 4/1987 | Kappelt et al. |
| 4,747,297 A | 5/1988 | Okayama et al. |

FOREIGN PATENT DOCUMENTS

| | | |
|---|---|---|
| JP | 09159598 | 6/1997 |
| JP | 2000028499 | 1/2000 |
| JP | 2002055029 | 2/2002 |
| JP | 2002-340778 | 11/2002 |
| JP | 2006506640 | 2/2006 |
| JP | 2006-194726 | 7/2006 |
| JP | 2006226808 | 8/2006 |
| JP | 2008157692 | 10/2008 |
| JP | 2008164419 | 7/2013 |
| SU | 828023 A1 | 5/1981 |

OTHER PUBLICATIONS

Fuzokusho E. Sanko, Heat Calculation (Transfer Tube), JIS B 8008-1, 2000, 4 pgs.

Reciprocating Internal Combustion Engines—Exhaust Emission Measurement—Part 1:Test-Bed Measurement of Gaseous and Particulate Emissions, 4 pgs., JIS B 8008-1, Apr. 20, 2009.

EXHAUST GAS ANALYSIS SYSTEM AND EXHAUST GAS ANALYSIS PROGRAM

CROSS-REFERENCE TO RELATED APPLICATIONS

This application is a continuation of application Ser. No. 13/824,507, filed Mar. 18, 2013, which is the U.S. national phase of PCT Application Number PCT/JP2011/070864, filed Sep. 13, 2011, which claims priority to Japanese Patent Application Number 2010-214546, filed Sep. 24, 2010, the disclosures of which are incorporated in their entirety by reference herein.

TECHNICAL FIELD

The present invention relates to an exhaust gas analysis system and an exhaust gas analysis program that measure particle concentration in exhaust gas emitted from an internal combustion engine such as a diesel engine.

BACKGROUND ART

As a system that measures particle concentration in exhaust gas emitted from a diesel engine, for example, as disclosed in JPA 2008-164419, there is a system that introduces exhaust gas into a particle counting device such as a CPC to count the number of particles.

Meanwhile, the exhaust gas is emitted in a high temperature state (e.g., 500° C.), and therefore in order to measure particle concentration in the exhaust gas, temperature of the exhaust gas should be reduced to a measurable temperature of the particle counting device. For this purpose, a possible method is that, by circulating the exhaust gas in the high temperature state in a pipe, the exhaust gas is cooled by thermal conduction of the pipe. However, this method has a problem that particles in the exhaust gas are attached to an inner wall of the pipe by thermal phoresis and the like, and consequently the number of particles in the exhaust gas introduced into the particle counting device is reduced to give rise to a measurement error.

For this reason, the conventional particle measurement system is, on an upstream side of the particle counting device, provided with a diluting device that dilutes sampled exhaust gas with low temperature diluting air (see FIG. 4 of JPA 2008-164419). On the basis of this, the particle measurement system is configured to reduce temperature of the exhaust gas to the measurable temperature of the particle counting device while preventing the particles from being attached to the inner wall of the pipe by the thermal phoresis and the like.

However, in the case where the particle measurement system is configured to be provided with the diluting device, the diluting device, peripheral devices (mass flow controller, pressure sensor, on/off valve, and the like), and pipes are required to cause problems that the system is increased in size, complexity, and cost. Also, by making the diluting device intervene, control of a diluting ratio, or the like, becomes a new error factor. Further, the system is increased in complexity, and therefore maintenance work on the system is also complicated.

SUMMARY OF INVENTION

Technical Problem

Therefore, the present invention is made in order to solve the above-described problems at once, and a main intended object thereof is to make it possible to accurately measure particle concentration even while cooling exhaust gas without dilution.

Solution to Problem

That is, an exhaust gas analysis system according to the present invention is characterized by being provided with: a particle concentration measurement device that measures concentration of particles contained in exhaust gas; a sampling cooling pipe that has an exhaust gas inlet introducing the exhaust gas and an exhaust gas outlet connected to the particle concentration measurement device, and cools the introduced exhaust gas to a measurable temperature of the particle concentration measurement device without dilution to guide the introduced exhaust gas; a temperature sensor that detects temperature of the exhaust gas flowing into the exhaust gas inlet; and a calculation device that uses a relational expression between the temperature of the exhaust gas and particle concentration at the exhaust gas inlet and the temperature of the exhaust gas and the particle concentration at the exhaust gas outlet, and from the detected temperature by the temperature sensor and the temperature of the exhaust gas introduced into the particle concentration measurement device, corrects the measured particle concentration by the particle concentration measurement device to calculate the particle concentration of the exhaust gas flowing into the exhaust gas inlet.

If so, the sampling cooling pipe cools the exhaust gas without dilution to guide the exhaust gas to the particle concentration measurement device, and therefore the need for a diluting device can be eliminated. This enables the system to be decreased in size, complexity, and cost. Also, the calculation device uses the predetermined relational expression to correct the measured particle concentration by the particle concentration measurement device, and therefore a measurement error caused by the attachment of particles to an inner wall of the sampling cooling pipe due to thermal phoresis and the like can be corrected. Accordingly, independently of a particle loss due to the thermal phoresis, the particle concentration in the exhaust gas can be accurately measured.

If temperature of the exhaust gas flowing out from the gas outlet keeps a constant temperature such as ambient temperature on the basis of cooling performance of the sampling cooling pipe, the temperature of the exhaust gas flowing into the particle concentration measurement device does not necessarily have to be detected. However, in the case where the temperature of the exhaust gas flowing out from the gas outlet is not a constant temperature, desirably, the exhaust gas analysis system is further provided with a second temperature sensor that detects the temperature of the exhaust gas flowing into the particle concentration measurement device, wherein the calculation device uses the detected temperature by the second temperature sensor as the temperature of the exhaust gas flowing into the particle concentration measurement device.

In order to simplify a configuration of the sampling cooling pipe, and also even in the case where a distance between an exhaust gas transfer pipe and the particle concentration measurement device is shortened, in order to be able to efficiently cool the collected exhaust gas, desirably, the sampling cooling pipe is adapted to be a single metal pipe, and spirally wound.

Thus, in the present invention the need for a diluting device, and peripheral devices and pipes associated with the diluting device can be eliminated, so that the system can be decreased in size and weight, and therefore can be preferably used as an in-car system Advantageous Effects of Invention According to the present invention configured as described, it becomes possible to accurately measure particle concentration even while cooling exhaust gas without dilution.

REFERENCE SIGNS LIST

Figure 1:
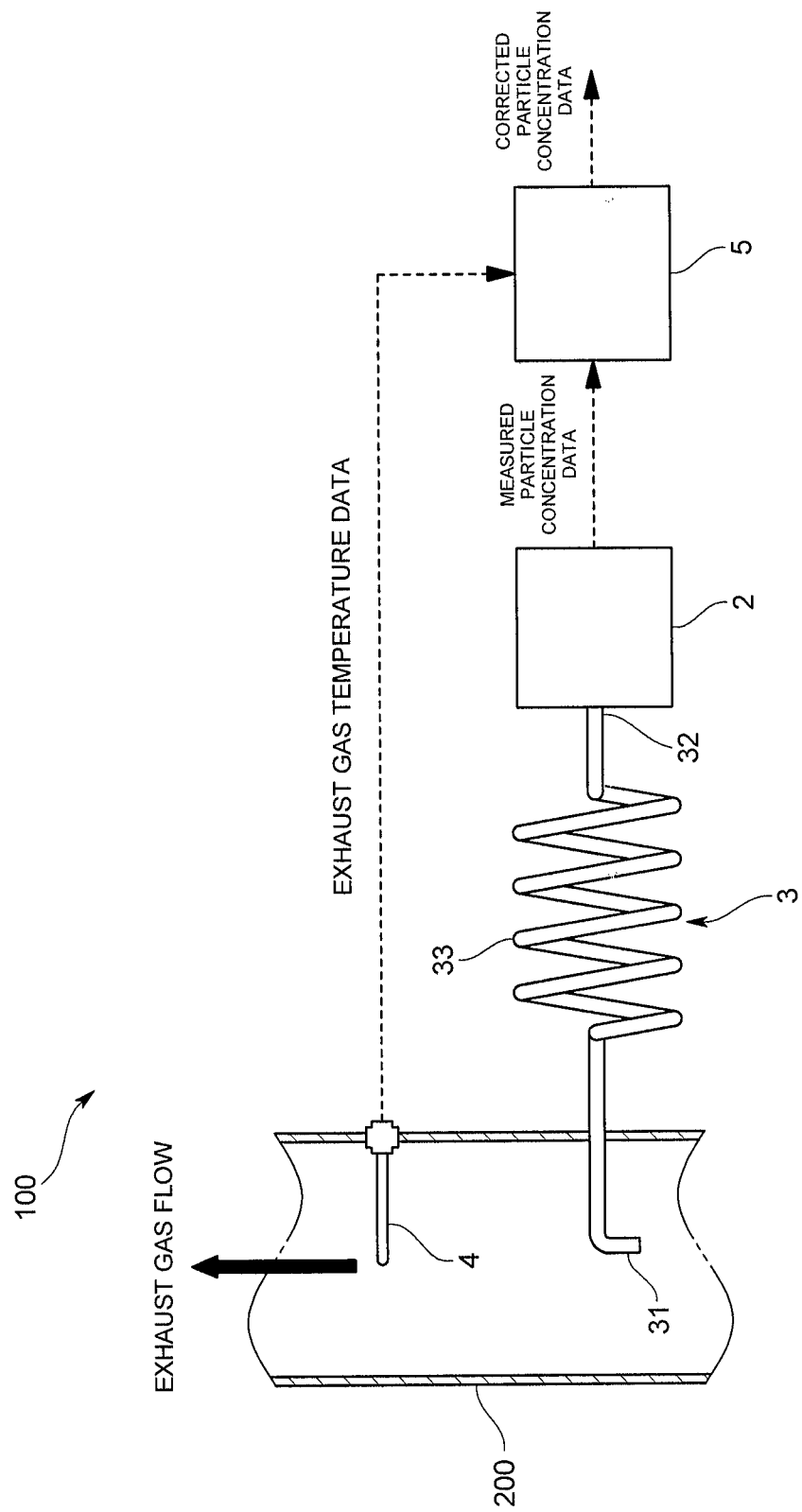
FIG. 1 is an overall schematic diagram schematically illustrating a configuration of an exhaust gas analysis system of the present embodiment.
Figure 2:
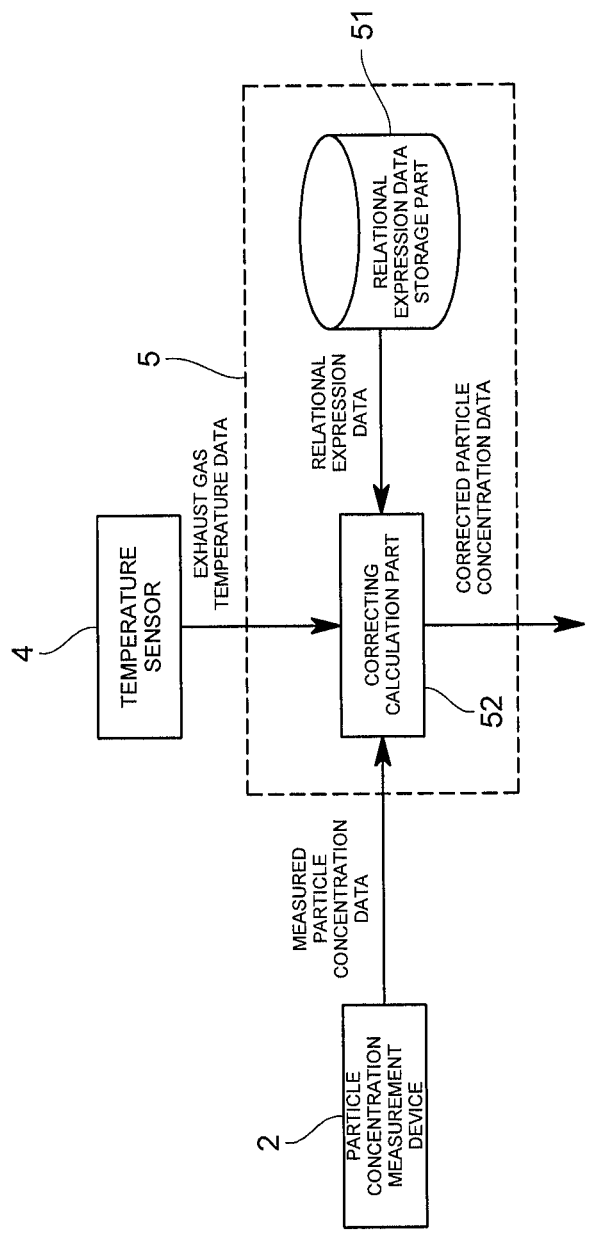
FIG. 2 is a diagram illustrating a functional configuration of a calculation device in the same embodiment.

100: Particle concentration measurement system
200: Exhaust pipe (exhaust gas transfer pipe)
2: Particle concentration measurement device
3: Sampling cooling pipe
31: Exhaust gas inlet
32: Exhaust gas outlet
4: Temperature sensor
5: Calculation device
51: Relational expression data storage part
52: Correcting calculation part
6: Second temperature sensor

DESCRIPTION OF EMBODIMENTS

In the following, one embodiment of an exhaust gas analysis system according to the present invention is described referring to the drawings.

An exhaust gas analysis system 100 according to the present embodiment is, as illustrated in FIG. 1, one that measures particle concentration of particulate matter (PM, hereinafter also simply referred to as particles) having a size of, for example, 1 □m or less contained in exhaust gas that flows through an exhaust pipe 200 serving as an exhaust gas transfer pipe connected to an internal combustion engine such as a diesel engine. Note that the particulate matter includes soot that is atomic carbon (soot), soluble organic fractions (SOF) from unburnt fuel and lubricating oil, sulfuric acid and sulfate, and the like. Also, the particle concentration refers to the number of particles (or number concentration), mass concentration of the particles, volume concentration of the particles, or the like. In the following embodiment, the case of measuring the number of particles is described.

Specifically, the exhaust gas analysis system 100 is, as illustrated in FIG. 1, provided with: a particle concentration measurement device 2 that measures concentration of particles contained in the exhaust gas; a sampling cooling pipe 3 that is connected to the exhaust pipe 200 and the particle concentration measurement device 2 and cools the high-temperature (e.g., 500 to 600° C.) exhaust gas flowing through the exhaust pipe 200 to be introduced the cooled exhaust gas into the particle concentration measurement device 2; a temperature sensor 4 that is provided with being inserted into the exhaust pipe 200 and detects temperature of the exhaust gas flowing through the exhaust pipe 200; and a calculation device 5 that corrects the measured particle concentration obtained by the particle concentration measurement device 2.

The particle concentration measurement device 2 is a particle number counting device that counts the number of particles contained in the exhaust gas sampled by the sampling cooling pipe 3. The particle number counting device in the present embodiment is, for example, a laser scattering-based condensation particle counter (CPC), and an operating temperature (measurable temperature) thereof is, for example, 5° C. to 35° C.

The sampling cooling pipe 3 is configured such that an exhaust gas inlet (exhaust gas introduction port) 31 that is one end opening thereof is provided inside the exhaust pipe 200 and also an exhaust gas outlet 32 that is the other end opening thereof is connected to the particle concentration measurement device 2. The sampling cooling pipe 3 is one that cools the collected exhaust gas to the measurable temperature (e.g., 5° C. to 35° C.) of the particle concentration measurement device 2 without dilution, and introduces the cooled exhaust gas into the particle concentration measurement device 2. In addition, the exhaust gas inlet 31 is provided so as to face to an upstream side with respect to a flow of the exhaust gas in the exhaust pipe 200.

Specifically, the sampling cooling pipe 3 is adapted to be a single metal pipe formed of, for example, stainless steel or the like, and between the exhaust gas inlet 31 and the exhaust gas outlet 32, formed with a cooling region 33 that is adapted to be spirally wound. The cooling region 33 is formed by spirally winding the pipe, and thereby an area of contact with surrounding air is made as large as possible to improve cooling performance. Also, in the sampling cooling pipe 3 in the present embodiment, a diameter, length, and the like of the pipe are set up such that the exhaust gas is cooled to ambient temperature (e.g., approximately 30° C.) at the gas outlet 32.

The temperature sensor 4 is a temperature sensor 4 such as a thermocouple, which is provided with being inserted from a side wall of the exhaust pipe 200 into the exhaust pipe 200. The temperature sensor 4 is one that is intended to detect gas temperature on an upstream side of the exhaust gas inlet 31 of the sampling cooling pipe 3, and in the present embodiment, to detect gas temperature near the exhaust gas inlet 31 of the sampling cooling pipe 3.

The calculation device 5 is one that is configured to include a digital or analog electric circuit having an unillustrated computer, memory, A/D converter, D/A converter, and the like, and may be a dedicated one, or one that is adapted to partially or entirely use a general-purpose computer such as a personal computer. Also, the calculation device 5 may be configured to, without use of the computer, fulfill functions as the respective parts only with an analog circuit, or may be, without the need of physical integration, one that includes a plurality of devices mutually connected with or without wires.

Further, by storing a predetermined program in the memory, and cooperatively operating the computer and its peripheral devices according to the program, the calculation device 5 fulfills functions as a relational expression data storage part 51, a correcting calculation part 52, and the like.

The relational expression data storage part 51 is one that stores relational expression data indicating a relational expression (Expression 1 below) related to a thermal phoresis-based loss, which is present between the exhaust gas temperature ($T_1$) and particle concentration ($C_1$) at the exhaust gas inlet 31 and the exhaust gas temperature ($T_2$) and the particle concentration ($C_2$) at the exhaust gas outlet 32. Note that the thermal phoresis-based loss is independent of a particle size. Specifically, the relational expression holds when a flow of the exhaust gas inside the sampling cooling pipe 3 is a turbulent flow, and in the case where a unit of $T_1$ and $T_2$ is kelvin [K], is expressed by:

[Expression 1]

$$\frac{C_2}{C_1} = \left(\frac{T_2}{T_1}\right)^{0.38} \quad (1)$$

($ISO8178-1$ ($JIS$ $B8008-1$)).

The correcting calculation part 52 obtains the preliminarily stored relational expression data from the relational expression data storage part 51, and also obtains detected temperature data from the temperature sensor 4 and measured particle concentration data from the particle concentration measurement device 2. Then, the correcting calculation part 52 uses Expression 2 below obtained from the relational expression data, and from the detected temperature by the temperature sensor 4 and the temperature (in the present embodiment, the ambient temperature) of the exhaust gas introduced into the particle concentration measurement device 2, corrects the measured particle concentration obtained by the particle concentration measurement device 2 in real time to calculate the particle concentration of the exhaust gas flowing through the exhaust pipe 200.

[Expression 2]

$$C_1 = C_2 X \left(\frac{T_2}{T_1}\right)^{-0.38} \quad (2)$$

Here, the correcting calculating part 52 substitutes the measured particle concentration by the particle concentration measurement device 2 into $C_2$, the detected temperature by the temperature sensor 4 into $T_1$, and the operable temperature of the particle concentration measurement device 2 (e.g., ambient temperature) into $T_2$. On the basis of this, the correcting calculation part 52 calculates the corrected particle concentration obtained by correcting in real time the measured particle concentration by the particle concentration measurement device 2 in consideration of concentration of particles attached to the sampling cooling pipe 3, and outputs the corrected particle concentration to output means such as a display.

Effect of the Present Embodiment

According to the exhaust gas analysis system 100 according to the present embodiment configured as described, the sampling cooling pipe 3 is connected to the exhaust pipe 200 and the particle concentration measurement device 2, and cools the collected exhaust gas to the measurable temperature without dilution to guide the cooled exhaust gas to the particle concentration measurement device 2, so that the need for a diluting device can be eliminated. This enables the system 100 to be decreased in size, complexity, and cost. Also, other problems caused by arranging the diluting device can also be solved.

Further, the calculation device 5 uses the relational expression indicated by Expression 1 to correct the measured particle concentration by the particle concentration measurement device 2, and therefore a measurement error caused by the attachment of particles to the inner wall of the sampling cooling pipe 3 due to the thermal phoresis and the like can be corrected. Accordingly, independently of the particle loss due to the thermal phoresis, the particle concentration in the exhaust gas can be accurately measured.

OTHER EMBODIMENTS

Note that the present invention is not limited to the above-described embodiment.

For example, in the above-described embodiment, on the assumption that the exhaust gas flowing through the sampling cooling pipe 3 is the turbulent flow, the above theoretical formula 1 is used; however, the present invention may use another theoretical formula, or an empirical formula or relational table prepared by experiment or the like. Also, in the case where the exhaust gas flowing through the sampling cooling pipe is a laminar flow as well, a corresponding theoretical or empirical formula is used. Besides, in the above-described embodiment, the relational expression related to the loss due to the thermal phoresis; however, the present invention may be adapted to use a relational expression taking into account, in addition to the loss due to the thermal phoresis, all particle losses caused by the passage through the sampling cooling pipe.

Figure 3:
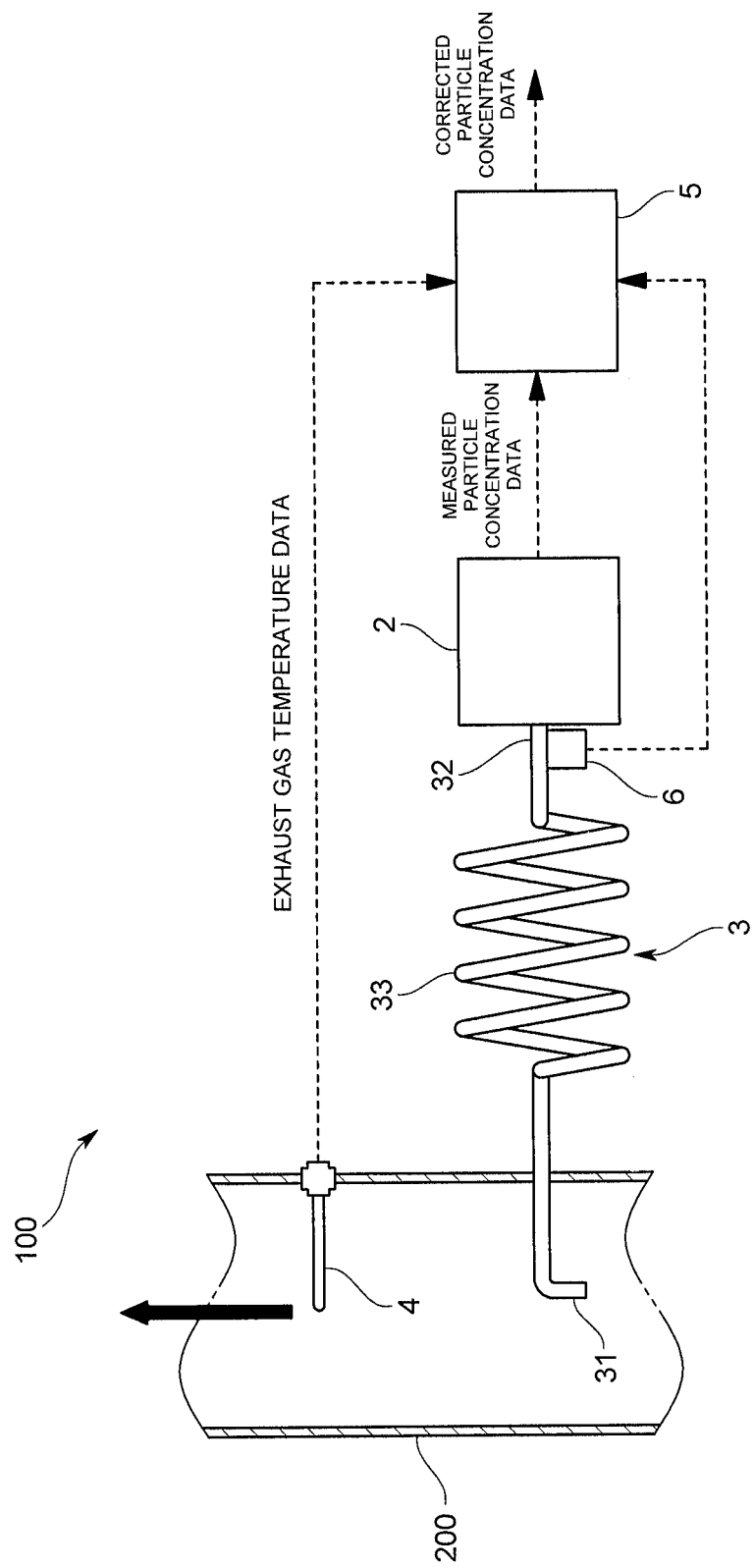
FIG. 3 is an overall schematic diagram schematically illustrating a configuration of an exhaust gas analysis system of a variation.

Also, in the above-described embodiment, on the assumption that the exhaust gas is cooled to the same temperature as the ambient temperature by the sampling cooling pipe 3, the ambient temperature is inputted to the calculation device 5 as $T_2$; however, besides, in the case where temperature after the cooling of the exhaust gas by the sampling cooling pipe 3 is different from the ambient temperature, or in another case, as illustrated in FIG. 3, the present invention may be adapted such that a second temperature sensor 6 that detects temperature of the exhaust gas flowing into the particle concentration measurement device 2 is further provided, and the calculation device 5 uses the detected temperature by the second temperature sensor 6 as the temperature ($T_2$) of the exhaust gas flowing into the particle concentration measurement device 2.

Further, as the exhaust gas transfer pipe, in addition to the exhaust pipe 200 of the internal combustion engine, a full flow diluting tunnel (full tunnel) that introduces a full amount of the exhaust gas flowing through the exhaust pipe 200 and dilutes the exhaust gas with diluting air may be used, or a split flow diluting tunnel (mini tunnel or micro tunnel) that collects part of the exhaust gas flowing through the exhaust pipe 200 in a split manner and dilutes the part of the exhaust gas with diluting air may be used. If so, it is not necessary to provide a diluting device in a stage subsequent to a diluting tunnel. In this case, particle concentration in the diluting tunnel can be calculated by correcting measured particle concentration obtained by the particle concentration measurement device 2, and from a dilution ratio of the diluting tunnel, particle concentration in the exhaust gas flowing through the exhaust pipe 200 can be calculated.

Still further, because the particle concentration measurement system in the above-described embodiment does not require a diluting device, the system can be decreased in size and weight, and also because a piping configuration is extremely simple, the system may be configured to be a on-board system.

In addition, in the above-described embodiment, the exhaust gas inlet of the sampling cooling pipe 3 is arranged inside the exhaust gas transfer pipe 200, and functions as the exhaust gas collecting port; however, besides, in the case where on an upstream side of the sampling cooling pipe, a diluting device is provided, the present invention is configured such that the exhaust gas inlet is connected to an outlet port of the diluting device and introduces exhaust gas diluted by the diluting device. That is, in the exhaust gas system in the above-described embodiment, on the upstream side of the exhaust gas inlet 31 of the sampling cooling pipe 3, an exhaust gas sampling part that collects the exhaust gas flowing through the exhaust gas transfer pipe 200 and the diluting device may be provided. In this case, the temperature sensor 4 is provided on a downstream side of the diluting device to detect temperature of the exhaust gas flowing into the exhaust gas inlet of the sampling cooling pipe 3. In this case, the calculation device 5 corrects measured particle concentration obtained by the particle concentration measurement device 2 to thereby calculate particle concentration of the exhaust gas flowing into the exhaust gas inlet 31 of the sampling cooling pipe 3, and further uses a dilution ratio of the diluting device to calculate particle concentration in the exhaust gas flowing through the exhaust pipe. Besides, the exhaust gas inlet of the sampling cooling pipe may be separately provided with an exhaust gas sampling part through piping. In this case, exhaust gas collected by the exhaust gas sampling part is introduced into the exhaust gas inlet.

Still in addition, in the case where a distance between the exhaust pipe and the particle concentration measurement device is sufficiently kept, the sampling cooling pipe is not required to be spirally wound, but may be formed in a straight pipe shape.

Further, the particle concentration measurement device in the above-described embodiment is one that measures the number of particles (or number concentration) in the exhaust gas; however, beside, the particle concentration measurement device may be one that measures mass concentration or volume concentration of particles.

Also, in the case where the particle concentration measurement device has a diluting device for the purpose of cooling and/or reduction of particle concentration, the present invention may be applied in order to cool the exhaust gas to a heat resistant temperature of the diluting device of the particle concentration measurement device.

Besides, it should be appreciated that the present invention is not limited to any of the above-described embodiment and variations, but can be variously modified without departing from the scope thereof.

INDUSTRIAL APPLICABILITY

According to the present invention, even while cooling exhaust gas without dilution, it becomes possible to accurately measure particle concentration.

What is claimed is:
1. An exhaust gas analysis system comprising:
a particle concentration measurement device that measures concentration of particles contained in exhaust gas from an exhaust pipe that is connected to an internal combustion engine;
a sampling cooling pipe that has an exhaust gas inlet to introduce the exhaust gas and an exhaust gas outlet connected to the particle concentration measurement device such that the exhaust gas flows through the sampling cooling pipe and enters the particle concentration measurement device via the exhaust gas outlet to guide the introduced exhaust gas;
a temperature sensor that detects temperature of the exhaust gas flowing into the exhaust gas inlet; and
a calculation device that uses a relational expression or relational table between the temperature of the exhaust gas and particle concentration at the exhaust gas inlet and the temperature of the exhaust gas and the particle concentration at the exhaust gas outlet, and from the detected temperature by the temperature sensor and the temperature of the exhaust gas introduced into the particle concentration measurement device, corrects the particle concentration measured by the particle concentration measurement device while the exhaust gas is flowing into the exhaust gas inlet and calculates the particle concentration of the exhaust gas flowing into the exhaust gas inlet.

2. The exhaust gas analysis system according to claim 1 further comprising a second temperature sensor that detects the temperature of the exhaust gas flowing into the particle concentration measurement device, wherein the calculation device uses the detected temperature by the second temperature sensor as the temperature of the exhaust gas flowing into the particle concentration measurement device.

3. The exhaust gas analysis system according to claim 1, wherein the sampling cooling pipe is adapted to be a single metal pipe, and is spirally wound.

4. The exhaust gas analysis system according to claim 1, wherein the sampling cooling pipe guides the introduced exhaust gas without dilution.

5. The exhaust gas analysis system according to claim 1 further comprising a diluting device that is provided on an upstream side of the sampling cooling pipe, wherein the exhaust gas inlet is connected to an outlet port of the diluting device and wherein the sampling cooling pipe guides exhaust gas diluted by the diluting device to the particle concentration measurement device.

6. An exhaust gas analysis system comprising:
a particle concentration measurement device that measures concentration of particles contained in exhaust gas from an exhaust pipe that is connected to an internal combustion engine;
an exhaust gas sampling part that has an exhaust gas inlet to introduce the exhaust gas and an exhaust gas outlet connected to the particle concentration measurement device;
a temperature sensor that detects temperature of the exhaust gas flowing into the exhaust gas inlet; and
a calculation device that uses a relational expression or relational table between the temperature of the exhaust gas and particle concentration at the exhaust gas inlet and the temperature of the exhaust gas and the particle concentration at the exhaust gas outlet, and from the detected temperature by the temperature sensor and the temperature of the exhaust gas introduced into the particle concentration measurement device, corrects the particle concentration measured by the particle concentration measurement device while the exhaust gas is flowing into the exhaust gas inlet and calculates the particle concentration of the exhaust gas flowing into the exhaust gas inlet.

7. A method of analyzing exhaust gas that measures concentration of particles contained in exhaust gas from an exhaust pipe connected to an internal combustion engine by using a particle concentration measurement device, the method comprising:
sampling exhaust gas from the particle concentration measurement device by using a gas sampling part having an exhaust gas inlet to introduce the exhaust gas and an exhaust gas outlet connected to the particle concentration measurement device;

detecting temperature of the exhaust gas flowing into the exhaust gas inlet by using a temperature sensor; and correcting the particle concentration measured by the particle concentration measurement device while the exhaust gas is flowing into the exhaust gas inlet by using the detected temperature and a temperature of the exhaust gas introduced into the particle concentration measurement device to calculate the particle concentration of the exhaust gas flowing into the exhaust gas inlet with a calculation device that has a relational expression or relational table between the temperature of exhaust gas and the particle concentration at the exhaust gas inlet and the temperature of the exhaust gas and the particle concentration at the exhaust gas outlet.

* * * * *